(12) United States Patent
Liburd et al.

(10) Patent No.: US 10,195,013 B2
(45) Date of Patent: *Feb. 5, 2019

(54) DRY PROSTHETIC HEART VALVE PACKAGING SYSTEM

(71) Applicant: Edwards Lifesciences Corporation, Irvine, CA (US)

(72) Inventors: Gregory G. Liburd, Riverside, CA (US); Abishek Gautam, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/935,483

(22) Filed: Mar. 26, 2018

(65) Prior Publication Data

US 2018/0206969 A1 Jul. 26, 2018

Related U.S. Application Data

(63) Continuation of application No. 15/400,934, filed on Jan. 6, 2017, now Pat. No. 9,937,030, which is a (Continued)

(51) Int. Cl.
*A61F 2/24* (2006.01)
*A61F 2/00* (2006.01)
(Continued)

(52) U.S. Cl.
CPC .......... *A61F 2/0095* (2013.01); *A01N 1/0263* (2013.01); *A61F 2/2412* (2013.01); *A61L 2/0094* (2013.01); *B65D 77/003* (2013.01); *B65D 77/20* (2013.01); *B65D 77/26* (2013.01); *A61L 2/20* (2013.01); *A61L 2/206* (2013.01);
(Continued)

(58) Field of Classification Search
CPC ...................................................... A61F 2/0095
See application file for complete search history.

(56) References Cited

U.S. PATENT DOCUMENTS 5,560,487 A * 10/1996 Starr ..................... A61F 2/0095
206/363
5,868,253 A * 2/1999 Krueger ................ A61F 2/0095
206/363

(Continued)

*Primary Examiner* — Donald R Spamer
(74) *Attorney, Agent, or Firm* — Thomas C. Richardson

(57) ABSTRACT

Packaging for prosthetic heart valves including an assembly for stabilizing dry prosthetic tissue implants such as heart valves during storage. The packaging assembly can be used for storing a bioprosthetic heart valve without a liquid preservative solution. The packaging assembly can comprise a holder comprising an engagement structure configured for removably attaching a bioprosthetic heart valve, the holder comprising a shaft. The packaging assembly can also include a storage tray comprising a cavity and an insert sized to provide a cap over the cavity of the storage tray, the insert comprising a slot having a closed central end and an open outer periphery. The shaft of the holder can be non-rotatably retained at the closed central end, wherein the insert defines a flat, generally planar disc comprising at least one of outward projections and flow passages.

20 Claims, 14 Drawing Sheets

Related U.S. Application Data continuation of application No. 14/221,101, filed on Mar. 20, 2014, now Pat. No. 9,539,080, which is a continuation of application No. 13/039,166, filed on Mar. 2, 2011, now Pat. No. 8,679,404.

(60) Provisional application No. 61/310,851, filed on Mar. 5, 2010.

(51) Int. Cl.
| | |
|---|---|
| *A01N 1/02* | (2006.01) |
| *A61L 2/00* | (2006.01) |
| *B65D 77/00* | (2006.01) |
| *B65D 77/20* | (2006.01) |
| *B65D 77/26* | (2006.01) |
| *A61L 2/20* | (2006.01) |

(52) U.S. Cl.
CPC ..... *A61L 2202/181* (2013.01); *A61L 2202/21* (2013.01)

(56) References Cited

U.S. PATENT DOCUMENTS

| | | | | |
|---|---|---|---|---|
| 6,126,007 | A * | 10/2000 | Kari | A61F 2/0095 206/363 |
| 6,416,547 | B1 * | 7/2002 | Erickson | A61F 2/0095 206/438 |
| 9,539,080 | B2 * | 1/2017 | Liburd | A01N 1/0263 |
| 9,937,030 | B2 * | 4/2018 | Liburd | A01N 1/0263 |

* cited by examiner

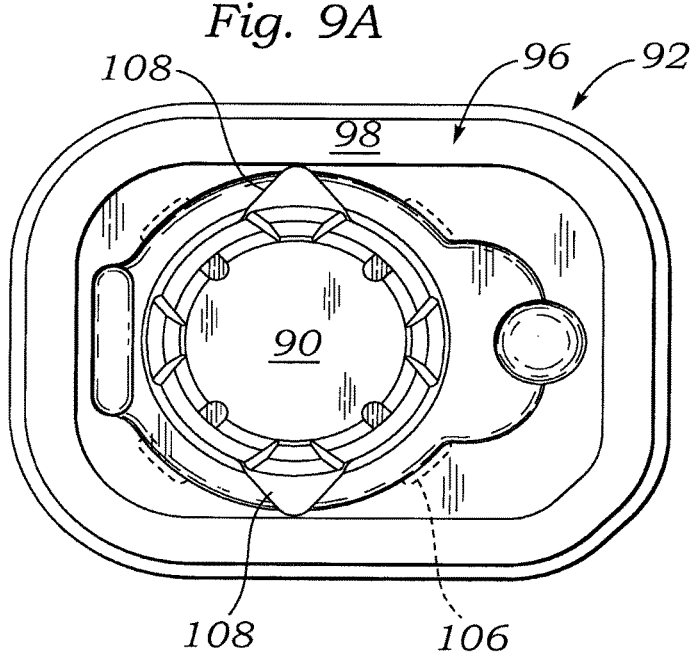
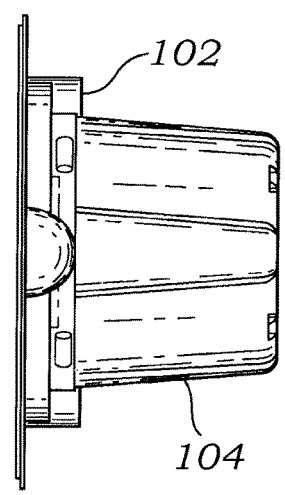
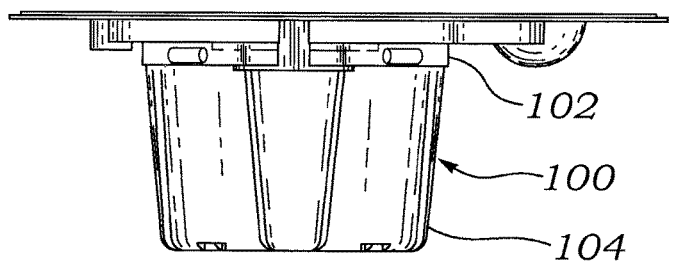

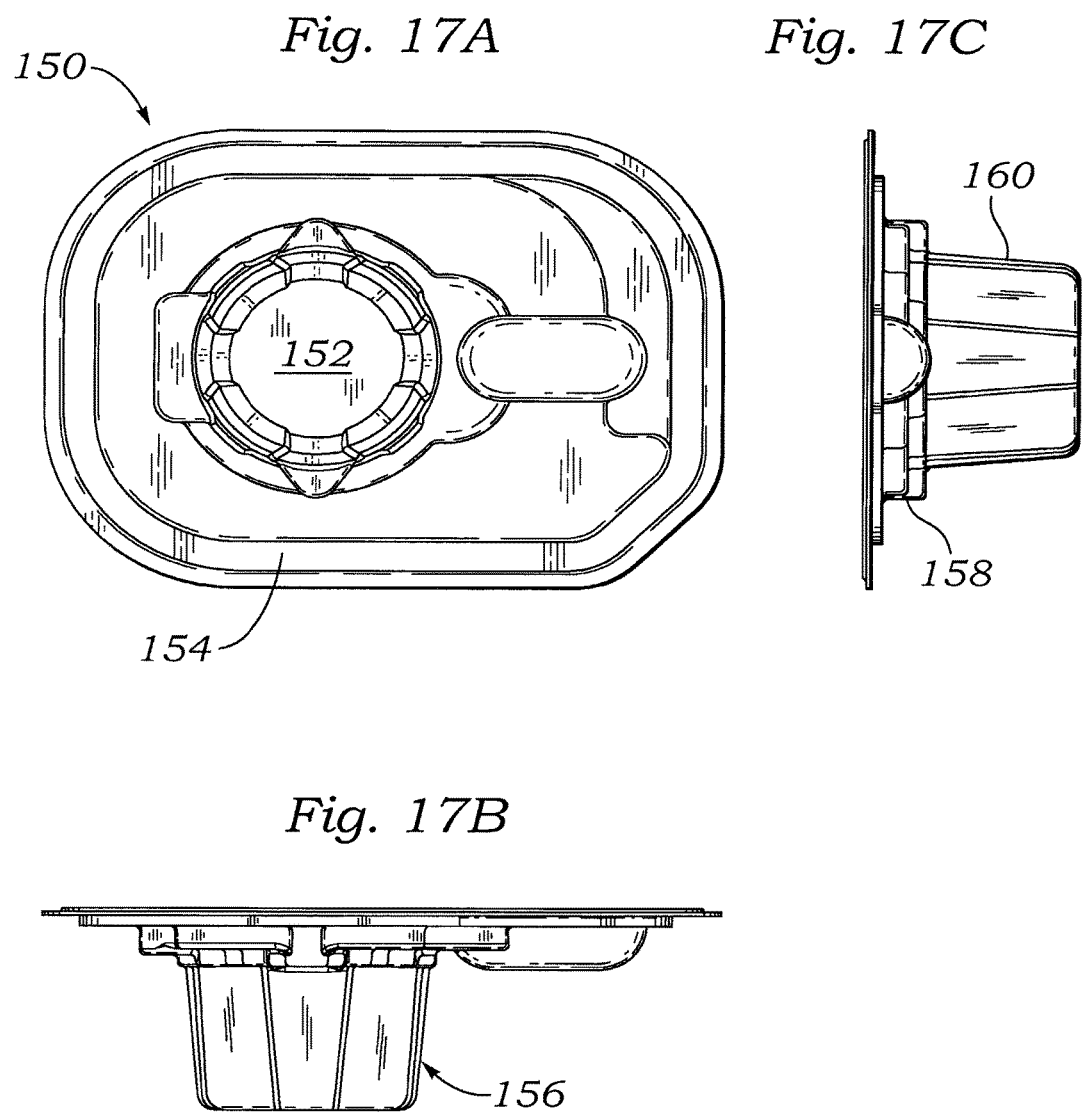

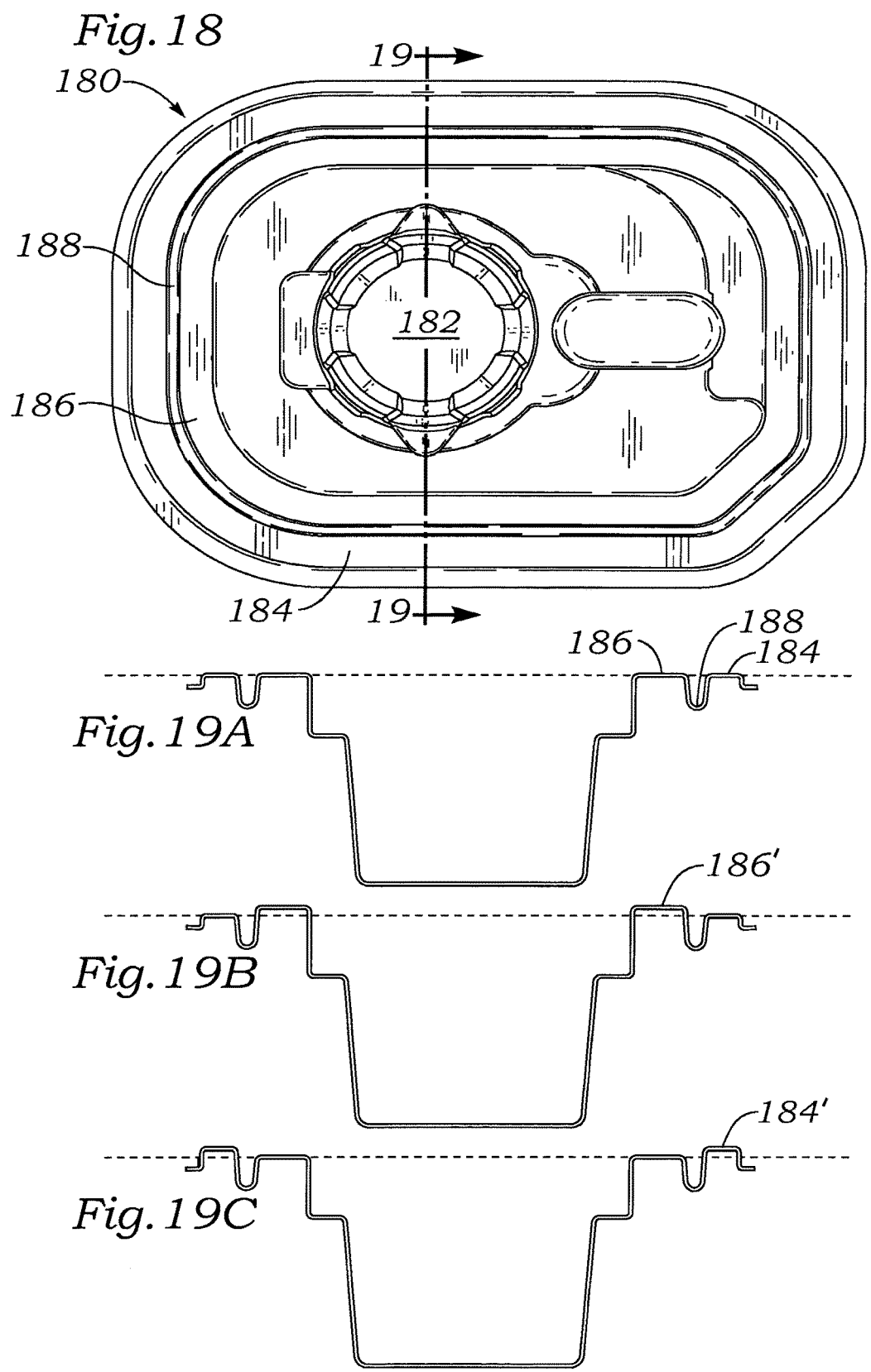

DRY PROSTHETIC HEART VALVE PACKAGING SYSTEM

CROSS REFERENCE TO RELATED APPLICATIONS

The present application is a continuation of U.S. patent application Ser. No. 15/400,934, filed Jan. 6, 2017, which is a continuation of U.S. patent application Ser. No. 14/221,101, filed Mar. 20, 2014, which is a continuation of U.S. patent application Ser. No. 13/039,166, filed Mar. 2, 2011, now U.S. Pat. No. 8,679,404, which claims the benefit of U.S. Provisional Application No. 61/310,851, filed Mar. 5, 2010, the entire disclosures of which are hereby incorporated herein by reference.

FIELD OF THE INVENTION

The present invention generally relates to packaging for prosthetic heart valves and, more particularly, to an assembly for sterile storage of dry prosthetic heart valves.

BACKGROUND OF THE INVENTION

Heart valve disease continues to be a significant cause of morbidity and mortality, resulting from a number of ailments including rheumatic fever and birth defects. Currently, the primary treatment of aortic valve disease is valve replacement. Worldwide, approximately 300,000 heart valve replacement surgeries are performed annually, and about one-half of these patients received mechanical heart valves, which are composed of rigid, synthetic materials. The remaining patients received bioprosthetic heart valve replacements, which utilize biologically derived tissues for flexible fluid occluding leaflets.

The most successful bioprosthetic materials for flexible leaflets are whole porcine valves and separate leaflets made from *bovine* pericardium stitched together to form a trileaflet valve. However, flexible leaflets formed of polymeric, fiber-reinforced, and other synthetic materials have also been proposed. The most common flexible leaflet valve construction includes three leaflets mounted to commissure posts around a peripheral non-expandable support structure with free edges that project toward an outflow direction and meet or coapt in the middle of the flowstream. A suture-permeable sewing ring is provided around the inflow end.

Bioprosthetic heart valves are conventionally packaged in jars filled with preserving solution for shipping and storage prior to use in the operating theater. To minimize the possibility of damage to the relatively delicate bioprosthetic heart valves, they are stabilized with bracketing structure to prevent them from striking the inside of the jar. Prior to implantation in a patient, the valve is removed from the jar and then rinsed in a shower or immersed and agitated in a bath. Prosthetic valves typically have a valve holder centrally located and sutured thereto, and the holders used for both are attached to the proximal end—to the inflow sewing ring for mitral valves and to the outflow commissure tips for aortic valves—so that an attached surgical delivery handle extends proximally out of the implant site.

Glutaraldehyde is widely used as a storage solution due to its sterilant properties but is known to contribute to calcification. Strategies to minimize glutaraldehyde content in the final product have been demonstrated to mitigate in vivo calcification.

One such strategy is to dehydrate the bioprosthetic tissue in a glycerol/ethanol mixture, sterilize with ethylene oxide, and package the final product "dry." This process circumvents the potential toxicity and calcification effects of glutaraldehyde as a sterilant and storage solution. There have been several methods proposed to use glycerine, alcohols, and combinations thereof as post-glutaraldehyde processing methods so that the resulting tissue is in a "dry" state rather than a wet state with excess glutaraldehyde. These approaches avoid the use of aqueous liquid aldehyde, or liquid sterilant as storage solutions for tissue and devices. Glycerol-based methods can be used for such storage, such as described in Parker et al. (Thorax 1978 33:638). Also, U.S. Pat. No. 6,534,004 (Chen et al.) describes the storage of bioprosthetic tissue in polyhydric alcohols such as glycerol.

In processes where the tissue is dehydrated in an ethanol/glycerol solution, the tissue may be sterilized by ethylene oxide, gamma irradiation, or electron beam irradiation. Ethylene oxide sterilization requires exposing the tissue to increased temperatures and water vapor which may generate oxidative damage in the tissue (Olde Damink, L H. et al. J Biomed Mater Res 1995 29:149). Gamma irradiation is known to generate significant reactive oxygen species in collagenous substrates which causes backbone scission and breakage of collagen fibrils (Ohan, M P et.al. J Biomed Mater Res A 2003 67:1188). This damage will lead to decreased mechanical and biochemical functionality in the tissue. Electron beam irradiation will also cleave the collagen backbone and lead to deterioration of the tissue structure and reactivity (Grant, R A et al. J Cell Sci 1970 7:387). Damage from oxidation during sterilization and/or storage may contribute to valve deterioration and structural failure.

U.S. Patent Publication No. 2009/0164005 to Dove, et al. presents solutions for certain detrimental changes within dehydrated tissue that can occur as a result of oxidation either from sterilization, atmospheric exposure during storage and handling, or from in vivo oxidation. Dove, et al. propose permanent capping of the aldehyde groups in the tissue (reductive amination) to help prevent significant oxidation of the tissue and lead to longer service lifetimes of the material. The process involves chemical capping of aldehydes (and other species) or otherwise neutralizing of the dehydrated tissue to prevent oxidation. Dove, et al. also describe the addition of chemicals (e.g., antioxidants) to the dehydration solution (e.g., ethanol/glycerol) to prevent oxidation of the tissue during sterilization (ethylene oxide, gamma irradiation, electron beam irradiation, etc.) and storage.

In view of the development of dry tissue heart valves, opportunities for alternative packaging for such valves arise that will save money and facilitate deployment in the operating field.

SUMMARY OF THE INVENTION

The present application discloses sterile packaging for dry bioprosthetic heart valves. New tissue treatment technology allows for packaging the tissue valves without liquid glutaraldehyde in a dry package. A double sterile barrier package disclosed herein contains, protects and preserves the dry bioprosthesis during ETO sterilization, transit and storage.

The present application provides packaging for prosthetic heart valves including an assembly for stabilizing dry prosthetic tissue implants such as heart valves during storage. The packaging assembly includes a double sterile barrier that permits gas sterilization of the tissue implant, and prevents oxidation of the implant during long-term storage. Tissue heart valves may be suspended within a cavity of an inner rigid tray and a cap may be placed over the cavity to limit movement of the valve therein. The inner tray is placed and sealed within an outer sterile barrier, such as another rigid tray or a flexible pouch. The outer sterile barrier may include a double seal so that a first gas-permeable seal can be closed and the contents gas sterilized, after which a second gas-impermeable seal can be closed to seal out any further atmospheric contact with the tissue implant. This keeps the implant from being oxidized. In one embodiment two nesting trays are used for redundant sterile barriers, and a gas-impermeable (e.g., foil) label is placed over the outer tray to provide the gas-impermeable seal.

In accordance with one method for packaging a dry tissue implant disclosed herein, a tray is provided having an upper surface and a cavity surrounded by an upper rim and descending downward therefrom. A technician places a dry tissue implant in the tray cavity and secures it from excessive movement therein. The technician engages a cap with the tray rim and over the cavity, the cap constraining the tissue implant in the cavity while providing gas flow passages for gas flow in and out of the cavity. The tray is then sealed by covering the tray upper surface with a gas-permeable lid, and the sealed tray and tissue implant therein are placed into a secondary container having a gas-permeable seal to form a dual barrier assembly. The dual barrier assembly is subjected to gas-based sterilization; and the secondary container is sealed with a gas-impermeable barrier to prevent gas transfer with the surrounding atmosphere. One way to seal the secondary container from the surrounding atmosphere comprises placing the secondary container within a gas-impermeable tertiary container such as a pouch having a gas-impermeable seal.

Another method disclosed herein is for packaging a dry tissue heart valve, and comprises the steps of:

providing a primary container having a gas-permeable seal;

placing a dry tissue heart valve and implant holder therefore in the primary container;

limiting movement of the heart valve in the primary container while providing gas flow passages around the heart valve;

sealing the primary container with the gas-permeable seal;

placing the sealed primary container and tissue implant therein into a secondary container and sealing the secondary container with a gas-permeable seal to form a dual barrier assembly;

subjecting the dual barrier assembly to gas-based sterilization; and sealing the secondary container with a gas-impermeable barrier to prevent gas transfer with the surrounding atmosphere.

Another method disclosed herein for packaging a dry aortic tissue heart valve includes first providing a tray having an upper surface and a cavity surrounded by an upper rim and descending downward therefrom. A technician secures a dry aortic tissue heart valve and implant holder therefore to a folding clam shell. The heart valve secured to the clam shell is placed in the tray cavity. The clam shell is sized and shaped to engage the tray rim over the cavity and limit vertical movement of the heart valve in the cavity while providing gas flow passages for gas flow in and out of the cavity. The tray is then sealed by covering the tray upper surface with a gas-permeable lid, and placed into a secondary container having a gas-permeable seal to form a dual barrier assembly. A technician subjects the dual barrier assembly to gas-based sterilization, and then seals the secondary container with a gas-impermeable barrier to prevent gas transfer with the surrounding atmosphere.

In any of the aforementioned methods, the secondary container may be a second tray having an upper surface and a cavity surrounded by an upper rim and descending downward therefrom. The second tray may be made of gas-impermeable material and the cavity is sized to receive the first tray, and the gas-impermeable seal may be a gas-impermeable label sealed to the upper rim of the second tray. In one embodiment, the second tray comprises a double flanged upper rim, and further includes a gas-permeable lid sealed to an inner flange and the gas-impermeable label sealed to an outer flange. Or, the secondary container may be a pouch of gas-impermeable material including a gas-impermeable seal, and the pouch may also include a gas-permeable seal outside of the gas-impermeable seal. Still further, the secondary container may be placed within a further gas-impermeable pouch of gas-impermeable material having a gas-impermeable seal.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIGS. 9A-9C are orthogonal views of the storage tray;

FIGS. 17A-17C are orthogonal views of a secondary storage tray sized to receive the first storage tray;

FIG. 18 is a plan view of an alternative secondary storage tray sized to receive the first storage tray and having double flanges;

FIGS. 19A-19C show several potential configurations of the relative heights of the double flanges in the tray of FIG. 18;

DETAILED DESCRIPTION OF THE PREFERRED EMBODIMENTS

The present invention provides an improved double barrier packaging system for dry prosthetic heart valves that effectively stabilizes the valve within a storage container without the need for a liquid preservative, provides an efficient vehicle for gas sterilization, and prevents oxidation of the valve during long-term storage.

Figure 1:
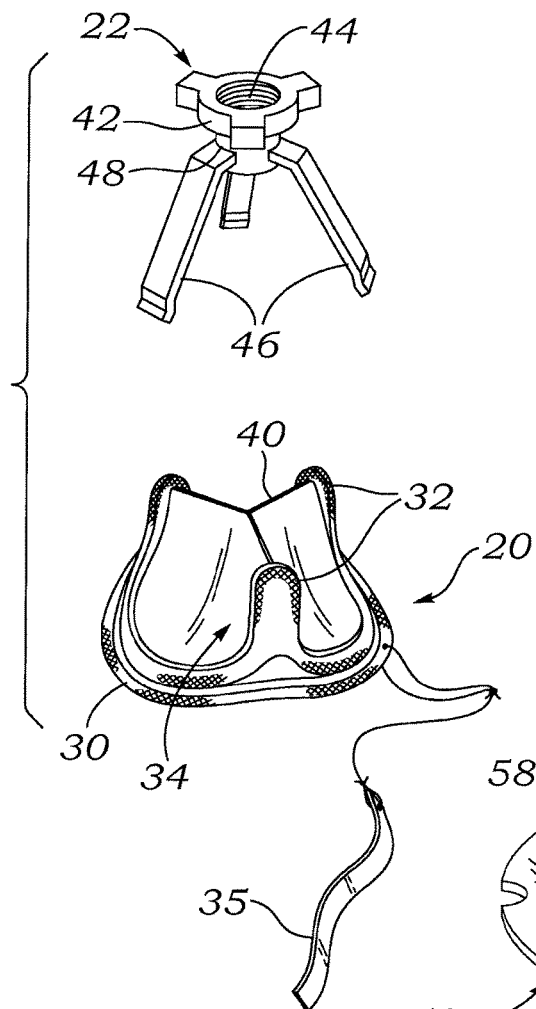
FIG. 1 is an exploded perspective view of an exemplary dry aortic tissue heart valve and a holder therefore.

FIG. 1 is an exploded perspective view of an exemplary aortic tissue heart valve 20 and a holder 22 therefore. The present application describes packaging systems that are particularly suitable for storing dry prosthetic tissue heart valves, and as such do not require liquid containment. The exemplary aortic tissue heart valve 20 includes a sewing ring 30 around an inflow end, a plurality of upstanding commissure posts 32 circumferentially distributed around the valve and projecting in an outflow direction, and a plurality of flexible leaflets 34 that provide fluid occluding surfaces for the one-way valve. Although not shown, additional components of the heart valve 20 typically include an inner stent and/or wire form support structure that provide a structural skeleton surrounding an inflow orifice and extending up the commissure posts 32. The inner components of the heart valve 20 may be made of suitable metal or plastic. An identification tag 35 secured to the sewing ring 30 with a length of suture provides a serial number representative of information regarding the type of heart valve 20 and other particularities about its manufacture, such as the date.

In the illustrated embodiment, the structural components of the heart valve 20 support each flexible leaflet 34 along a cusp edge and along two commissure edges. A free edge 40 of each leaflet 34 extends inward toward a central flow orifice and coapts, or mates, with the free edges of the other leaflets, as shown. The most common configuration of prosthetic aortic tissue heart valve has three flexible leaflets 34 supported by three upstanding commissure posts 32, although different configurations are conceivable.

Flexible leaflets 34 may be made from a variety of materials, though bioprosthetic tissue is considered to be most effective. The most common bioprosthetic tissue is *bovine* pericardium, where the individual leaflets 34 are cut from pericardial sac of a cow. An exemplary dry tissue heart valve that may be stored without need for liquid preservatives in the packaging systems described herein may be obtained from Edwards Lifesciences of Irvine, Calif. One preferred tissue treatment process includes applying a calcification mitigant such as a capping agent or an antioxidant to the tissue to specifically inhibit oxidation in dehydrated tissue and reduce in vivo calcification. In one method, tissue leaflets in assembled bioprosthetic heart valves are pretreated with an aldehyde capping agent prior to dehydration and sterilization. Exemplary processes are described in U.S. Patent Application No. 20090164005 to Dove, et al., filed Jun. 25, 2009, the disclosure of which is expressly incorporated herein by reference.

Figure 2:
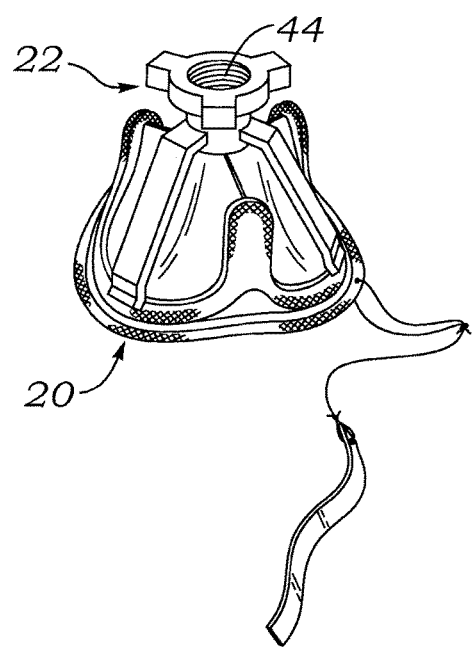
FIG. 2 is an assembled perspective of the heart valve and holder.

With reference still to FIG. 1, the exemplary holder 22 includes a central hub structure 42 having a bore with internal threads 44, and a plurality of outwardly and downwardly angled legs 46. A narrow neck region 48 separates the hub structure 42 and the upper end of the legs 46. The legs 46 are arranged to contact and engage the valve sewing ring 30 intermediate each pair of adjacent commissure posts 32, as seen in the assembled perspective of FIG. 2. That is, the legs 46 contact the cusp regions of the heart valve 20. Although not shown, one configuration for connecting the legs 46 to the sewing ring 30 includes attachment sutures that loop through the suture-permeable material of the sewing ring 30 and tie off on the holder 22, such as on one of the legs 46. During implant, the surgeon manipulates a handle (not shown) screwed into the threaded bore 44 and advances the aortic heart valve 20 into implant position at the aortic annulus. Once in position, and typically after anchoring sutures have been deployed between the sewing ring 30 and the surrounding native annulus, the surgeon severs the attachment sutures coupling the holder 22 to the valve 20, and removes the holder and handle.

Figure 3:
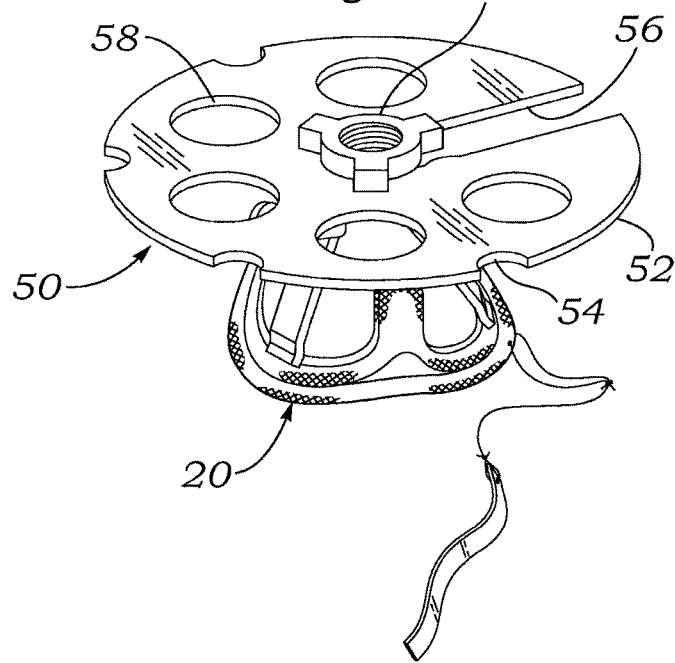
FIG. 3 is a perspective view of a subassembly of the heart valve and holder coupled to a disc-shaped storage clip.

FIG. 3 is a perspective view of a subassembly of the aortic heart valve 20 and holder 22 coupled to a disc-shaped storage clip 50. The clip 50 is desirably planar and has a substantially circular outer periphery 52 interrupted by a plurality of semi-circular notches 54 and a radial slot 56. The clip 50 further includes a plurality of circular through holes 58. The radial slot 56 terminates in a central circular aperture (not shown) sized approximately the same as the narrow neck region 48 of the holder 22. The width of the radial slot 56 is slightly smaller than the neck region 48, such that the holder 22 may be pushed inward along the slot and snapped into the central aperture, with the hub structure 42 above the clip 50. As will be seen below, the clip 50 caps a cavity of a storage tray in which the heart valve is stored to stabilize the valve therein.

Figure 4:
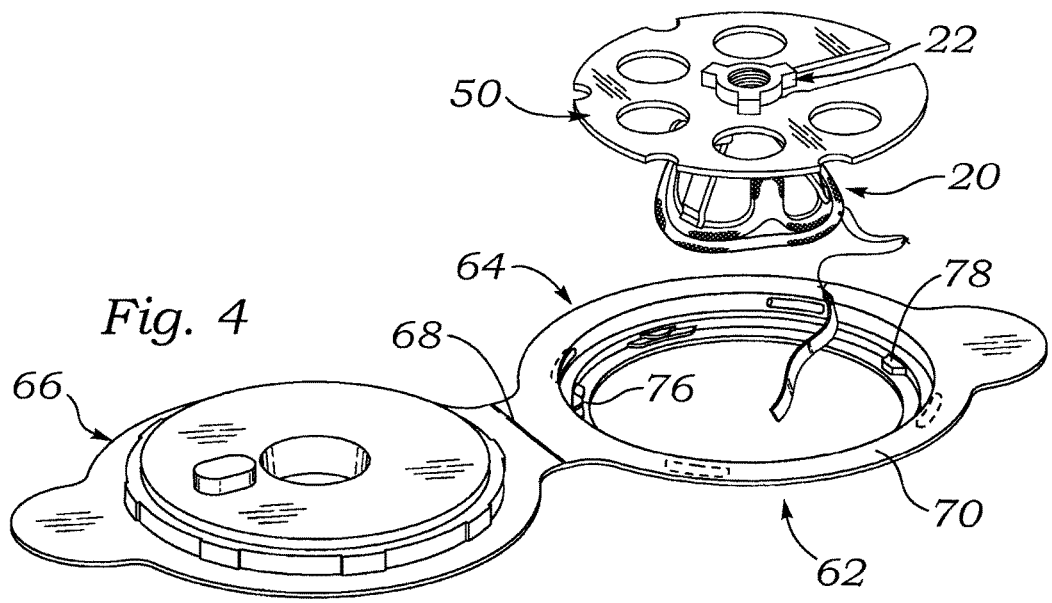
FIGS. 4 and 5 are exploded and assembled perspective views of the heart valve/holder and clip subassembly positioned within a lower half of a clam shell member used to stabilize the heart valve during storage.
Figure 5:
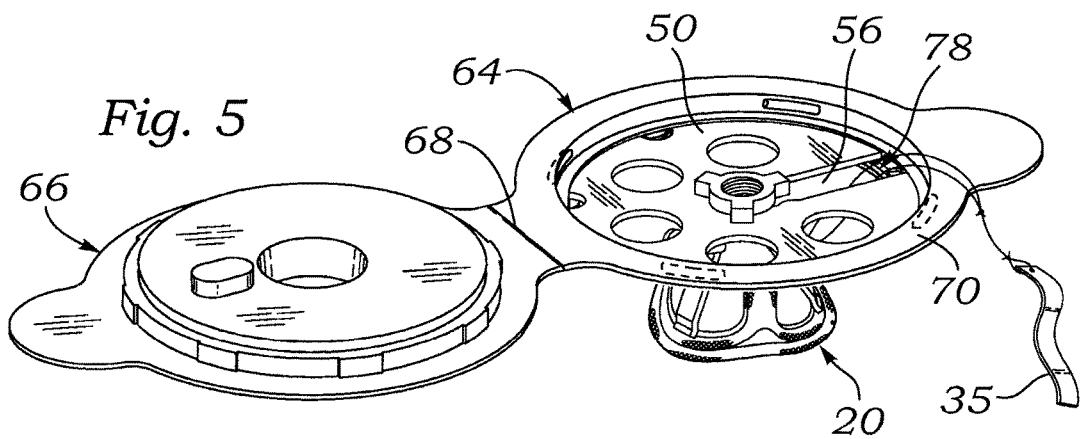

FIGS. 4 and 5 illustrate a clam shell member 62 used to stabilize the heart valve 20 during storage. The subassembly of the valve 20, holder 22, and clip 50 is shown in FIG. 4 exploded above a lower half 64 of the clam shell member 62, and positioned within the lower half in FIG. 5. The clam shell member 62 is desirably constructed of a transparent molded material, such as a polyethylene terephthalate copolymer (PETG).

Figure 6:
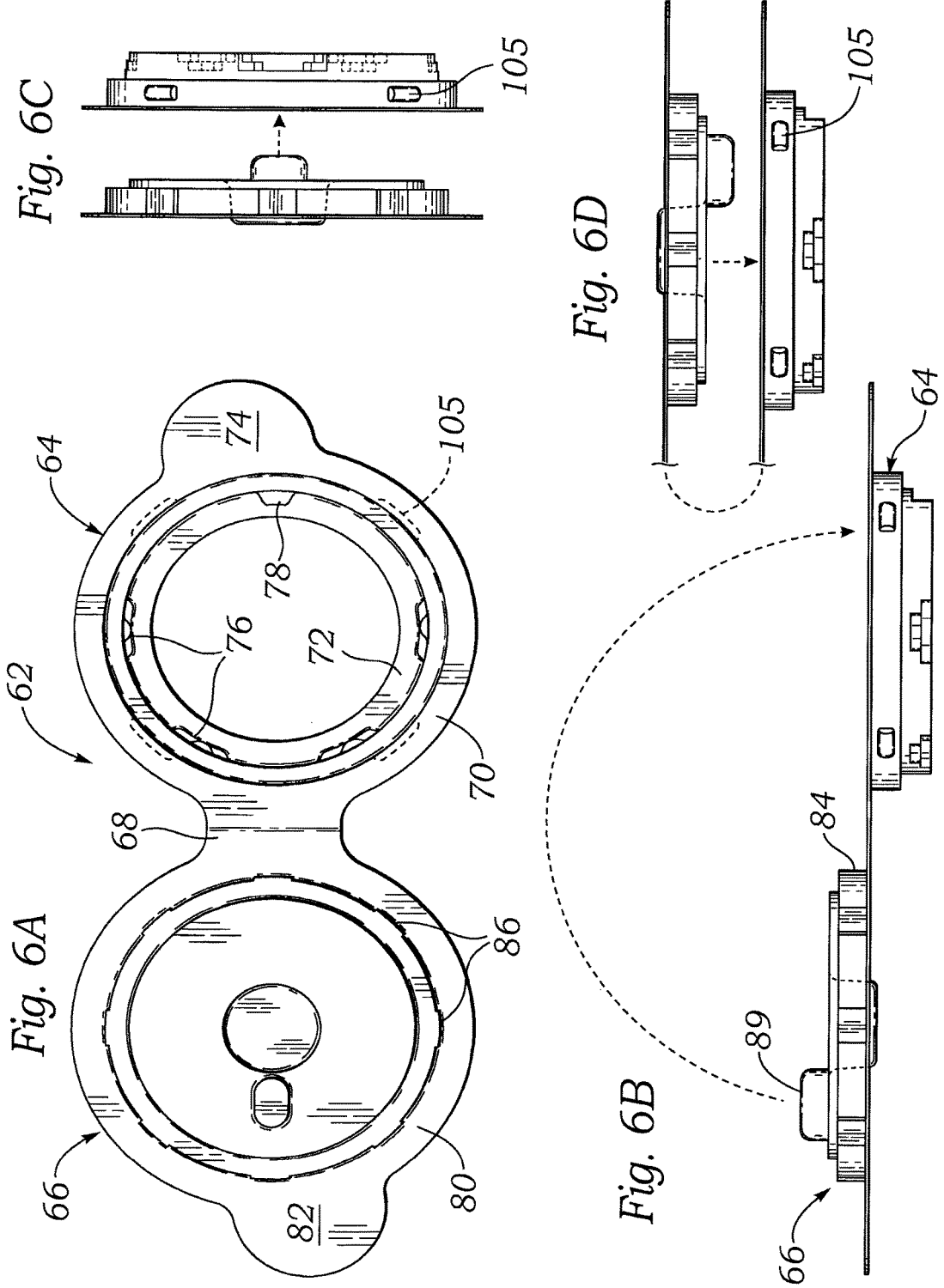
FIGS. 6A-6D are orthogonal views of the clam shell member.

The clam shell member 62 includes the lower half 64 hinged to an upper half 66. As seen also in FIGS. 6A-6C, clam shell member 62 is desirably molded from clear plastic and the two halves connect at a living hinge 68. The lower half 64 includes an annular rim 70 above and surrounding a circular aperture defined by a lower ledge 72 and having a finger tab 74 extending away from the hinge 68. A plurality of separate molded features project inward from the annular rim 70 above the lower ledge 72, including four clip supports 76 and an anti-rotation projection 78. As seen in FIG. 5, the generally circular clip 50 is sized to fit within the annular rim 70 and rest on the clip supports 76. The circumferential width of the anti-rotation projection 78 permits it to fit closely within the radial slot 56 of the clip 50, thus preventing rotation of the clip in the clam shell member 62.

Figure 7:
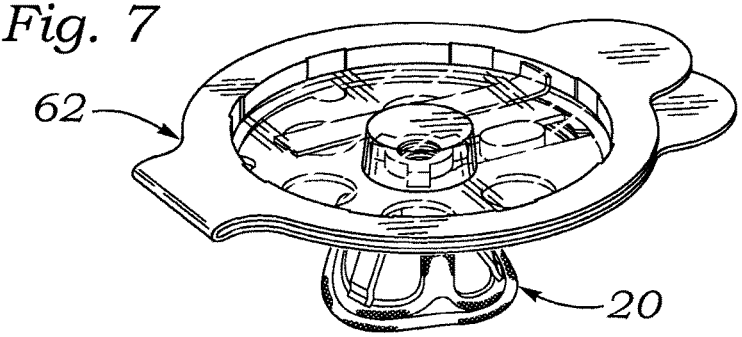
FIG. 7 is a perspective view of the heart valve/holder and clip subassembly positioned in the clam shell member with an upper half folded closed over the lower half.

The clam shell member upper half 66 has an outer ledge 80 including a finger tab 82 extending away from the hinge 68. An inner generally cylindrical boss 84 fits within and mates with the inner surface features of the lower half annular rim 70. In particular, a series of projections 86 on the cylindrical boss 84 frictionally engage the inner surface of the lower half annular rim 70. The engagement of the projections 86 with the inside of the rim 70 desirably provides an audible and tactile click or snap upon closing the halves of the clam shell member 62. Prior to closing the clam shell member 62, the identification tag 35 may be positioned on the circular clip 50 with the serial number facing upward for greater visibility and to prevent the tag from contacting and potentially damaging the heart valve 20 during storage. The final assembly of the valve/holder/clip in the closed clam shell member 62 is seen in FIG. 7. As an additional locking feature, a downward projection 89 on the upper half 66 fits closely into the mid-portion of the radial slot 56 of the clip 50, thus further limiting movement of the clip in the clam shell member 62.

Figure 8:
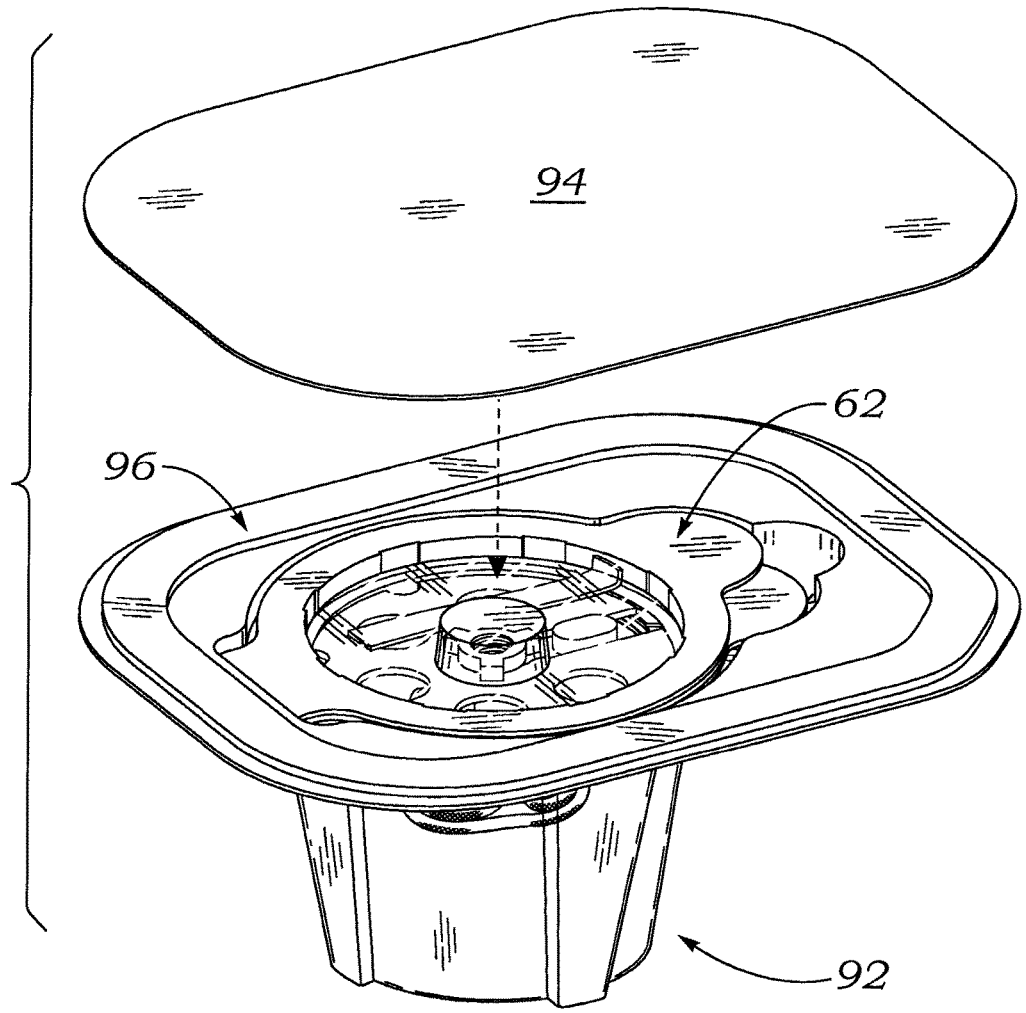
FIG. 8 illustrates the assembly of FIG. 7 placed within a cavity of a storage tray, and a gas-permeable lid for sealing over an upper surface of the tray.

FIG. 8 then illustrates the assembly of FIG. 7 placed within a cavity 90 of a storage tray 92, whereupon a gas-permeable lid 94 having an outer band of adhesive 95 seals over an upper surface 96 of the tray 92. FIGS. 9A-9C are orthogonal views of the storage tray 92 illustrating a flat, horizontal outer rim 98 defining the tray upper surface 96, and surrounding the cavity 90. The cavity 90 is formed by the inner contours of a container portion 100 extending downwardly from the outer rim 98. The container portion 100 includes a stepped ledge 102 on an upper end and a lower trough 104. When the assembly of FIG. 7 is placed within the cavity 90, the clam shell member 62 rests on the stepped ledge 102 and the heart valve 20 extends downward within the lower trough 104. Note in FIG. 6C, external features 105 on the lower half 64 of the clam shell member 62 which frictionally engage the internal features 106 on the stepped ledge 102 of the storage tray 92. Engagement between the features 105, 106 nominally retains the clam shell member 62 in the storage tray 92, and prevents the clam shell member from falling out if the tray is inverted but presents minimal difficulty to a user removing the clam shell member using the thumb tabs. Preferably, the features 105, 106 engage with a snap or tactile feedback. Because the clam shell member 62 secures the circular clip 50, which in turn secures the valve/holder combination, the heart valve 20 is stably suspended within the cavity 90 without touching the sides of the tray 92.

Figure 10:
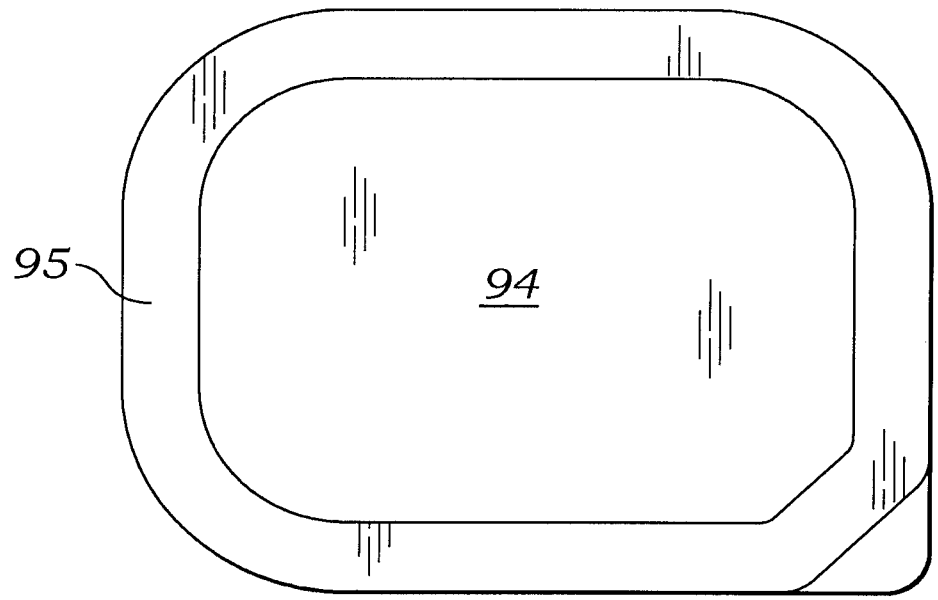
FIG. 10 is a plan view of the underside of a gas-permeable lid for sealing over an upper surface of the storage tray.

FIG. 10 shows the gas-permeable lid 94 that seals over the upper surface 96 of the storage tray 92. More specifically, the outer rim 98 forms a flange to which the band of adhesive 95 on the lid 94 may be adhered. Preferably, the lid 94 is closely dimensioned to the perimeter of the outer rim 98, and the band of adhesive 95 is a pressure-seal or a heat seal adhesive to facilitate sealing under pressure and/or temperature. The material of the lid 94 is breathable, or gas-permeable, to provide for gas sterilization of the contents sealed within the tray 92, in particular the dry tissue heart valve 20. One suitable gas-permeable material is a sheet of high-density polyethylene fibers, which is difficult to tear but can easily be cut with scissors. The material is highly breathable and water vapor and gases can pass through the fibers, but not liquid water. For instance, various Tyvek materials from DuPont may be used. Also, exemplary hot-melt adhesives used to secure the lid 94 to the tray 92 may be obtained from Perfecseal or Oliver-Tolas, for example. Such a material permits sterilization of the tray contents using Ethylene Oxide (ETO), which gradually passes through the lid 94 to the interior tray. The lid 94 presents a sterile barrier and prevents ingress of microorganisms. The tray 92 is desirably a molded material, such as a polyethylene terephthalate copolymer (PETG), that provides rigidity and protection from jostling and external pressures. Various medical storage materials and packaging suitable for assembly of components of the present application are available from companies such as Dupont, Perfecseal, Oliver-Tolas, and Mangan.

Ethylene oxide (ETO), also called oxirane, is the organic compound with the formula $C_2H_4O$. It is commonly handled and shipped as a refrigerated liquid. ETO is often used as sterilant because it kills bacteria (and their endospores), mold, and fungi. It is used to sterilize substances that would be damaged by high temperature techniques such as pasteurization or autoclaving. Ethylene oxide is widely used to sterilize the majority of medical supplies such as bandages, sutures, and surgical implements in a traditional chamber sterilization method, where a chamber has most of the oxygen removed (to prevent an explosion) and then is flooded with a mixture of ethylene oxide and other gases that are later aerated.

Certain features of the clam shell member 62 and storage tray 92 facilitate gas sterilization, such as with ETO. Specifically, the clam shell member 62 provides a cap that limits vertical movement of the heart valve 20 in the tray cavity 90 while providing gas flow passages for gas flow in and out of the cavity. Good flow of sterilization gas in and out of the cavity 90 facilitates complete and rapid sterilization of the tissue heart valve 20. First of all, the clam shell member 62 sits on the stepped ledge 102, and a pair of diametrically opposed gas flow channels 108 provide openings between the two elements for passage of gas into the cavity 90. In addition, the engagement between the lower and upper halves 64, 66 of the clam shell member 62 permits gas to flow therethrough, around the upper end of the valve 20. More specifically, the circular clip 50 is supported by the four clip supports 76 above the lower ledge 72, allowing gas to flow around the clip 50. Furthermore, the clip 50 includes large circular through holes 58 for direct gas flow therethrough. In short, the stable yet discontinuous engagement of the packaging elements permits good gas flow in and around the tissue heart valve 20.

Figure 12:
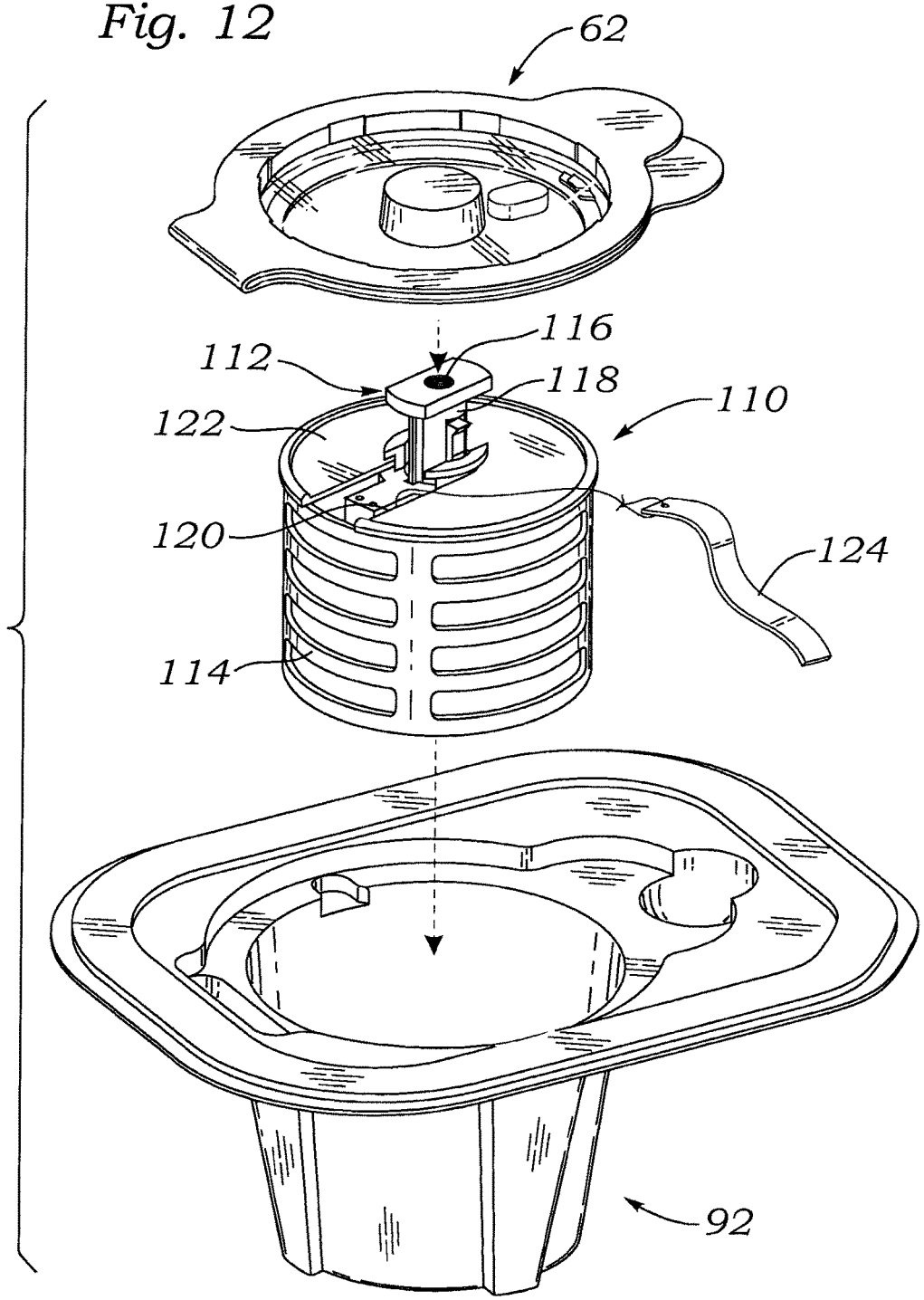
FIG. 12 is an exploded perspective view of the aforementioned storage tray and clam shell member on either side of an exemplary dry mitral tissue heart valve subassembly including a holder and protective cage.

FIGS. 12-16 illustrates an alternative packaging system for mitral heart valves. FIG. 12 is an exploded perspective view of the same storage tray 92 and closed clam shell member 62 for aortic valve storage on either side of an exemplary mitral tissue heart valve subassembly 110, including a holder 112 and a protective cage 114. In contrast with aortic valves, the holder 112 for mitral valves attaches to the inflow end of the valve, typically to the sewing ring. Although not shown, the holder 112 includes engagement structure, such as attachment sutures, for removably attaching to the sewing ring of the mitral heart valve.

The holder 112 may take a number of forms, but typically includes an upper bore 116 having internal threads for attaching a delivery handle. One exemplary holder 112 that may be used is available as the TRICENTRIX® holder system for use with the Carpentier-Edwards® PERIMOUNT Plus® mitral pericardial valve from Edwards Lifesciences of Irvine, Calif. A shaft 118 of the holder 112 fits closely within a radial slot 120 in a clip member 122 attached to the upper end of the protective cage 114. An identification tag 124 attached to the heart valve sewing ring with a suture passes upward through the radial slot 120. The holder 112 stabilizes the mitral heart valve in a fixed position with the protective cage 114, which in turn prevents the outflow end of the heart valve from advert contact with the inner walls of tray 92, and later contact with external surfaces and instruments in the operating room when the heart valve is removed for implantation.

Figure 13:
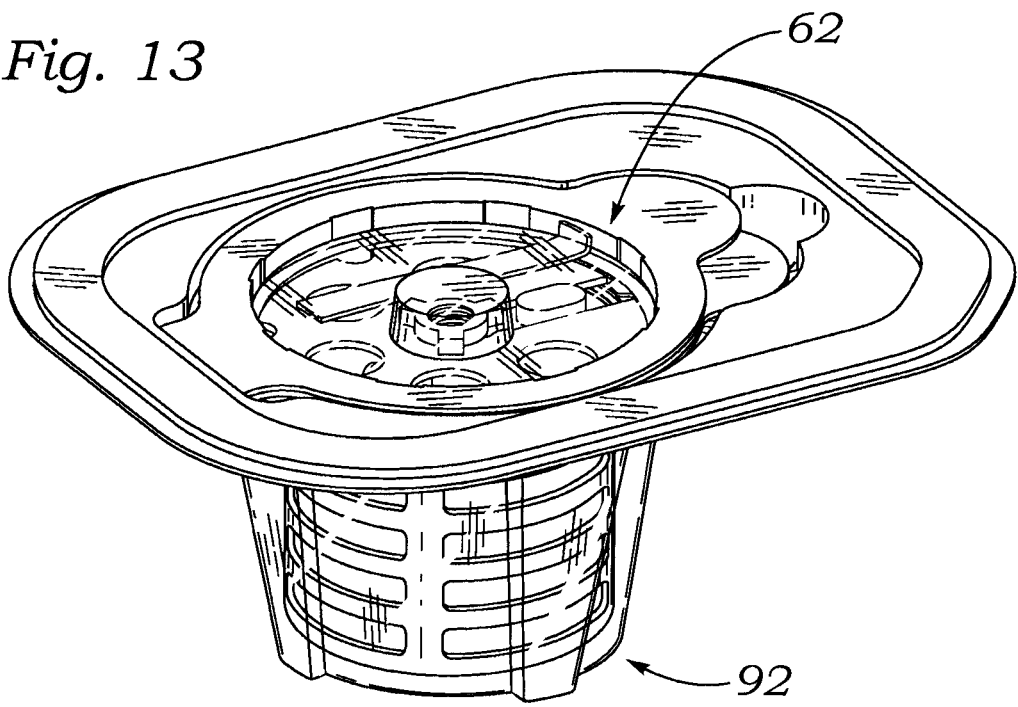
FIG. 13 shows the mitral tissue heart valve subassembly seated within the cavity of the storage tray with the clam shell member positioned thereover to limit vertical movement of the subassembly in the cavity.

FIG. 13 shows the mitral tissue heart valve subassembly 110 seated within the cavity of the storage tray 92 with the clam shell member 62 positioned thereover. When pressed down into the cavity of the storage tray 92, the clam shell member 62 acts as a cap on the cavity to limit vertical movement of the heart valve subassembly 110 therein. As before, frictional engagement between the external features 105 (FIGS. 6C and 6D) on the lower half 64 of the clam shell member 62 and internal features 106 on the stepped ledge 102 of the storage tray 92 retains the clam shell member as a cap over the heart valve subassembly 110.

Figure 14:
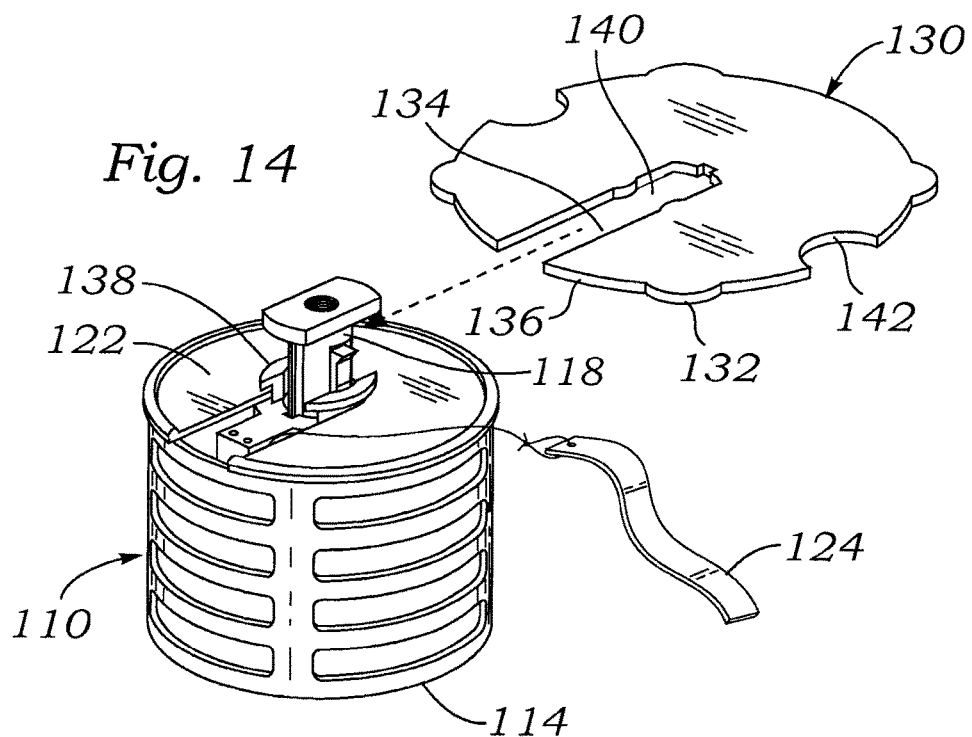
FIG. 14 shows an alternative disc-shaped insert prior to coupling to the mitral tissue heart valve subassembly.
Figure 15:
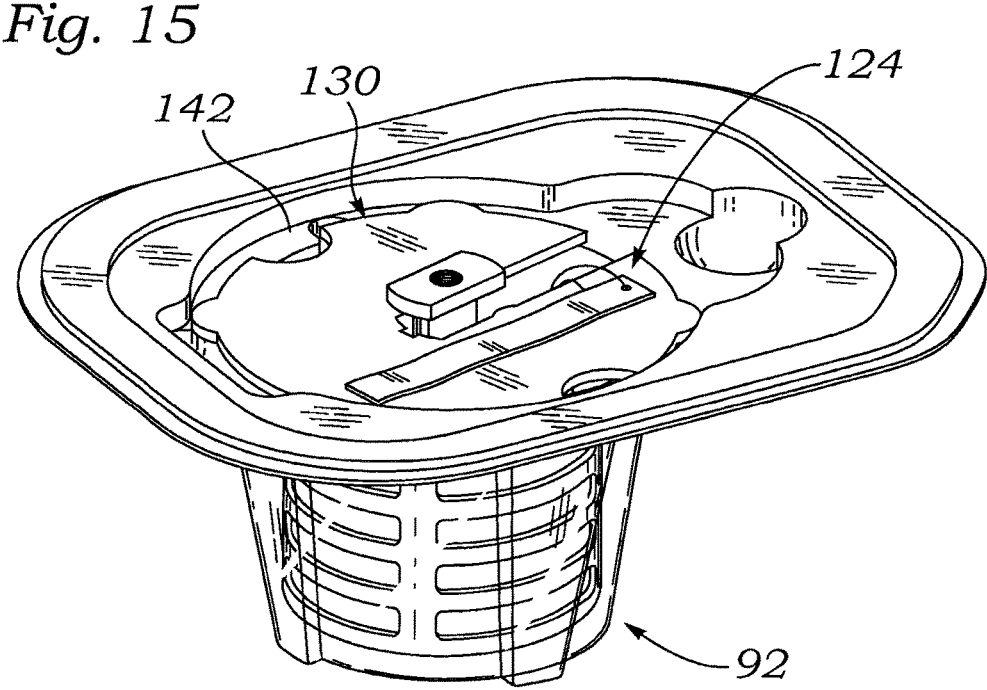
FIG. 15 shows the combination of the disc-shaped insert and mitral tissue heart valve subassembly seated within the cavity of the storage tray.

As an alternative to the clam shell member 62, a disc-shaped insert 130 may be used to provide a cap over the cavity storage tray 92, as seen in FIG. 14. The insert 130 defines a flat, generally planar disc having four outward protections 132 and a radial slot 134 open to an outer periphery 136. The insert 130 is desirably formed of a suitable molded plastic, such as a high-density polyethylene (HDPE). The slot 134 fits closely around a non-circular portion of the holder shaft 118 and includes a narrowed region 140 that retains the shaft 118 at a closed central end of the slot 134. Once the insert 130 has been snapped onto the heart valve subassembly 110, the combination may be lowered into the cavity of the storage tray 92, as seen in FIG. 15. The outward protections 132 snap under the internal features 106 on the stepped ledge 102 of the storage tray 92 such that the insert 130 caps the cavity over the heart valve subassembly 110. Flow passages 142 align with the flow channels 108 provided in the storage tray 92 and facilitate sterilizing gas flow between the insert 130 and tray. As before, the identification tag 124 of the mitral heart valve may be positioned over the top of the insert 130 so that the serial number is visible from above without removing the heart valve subassembly 110 from the tray 92. Also, it should be noted that the insert 130 engages the tray 92 in a non-rotating manner, as does the insert slot 134 around the non-circular holder shaft 118, which means that the valve holder 112 is held stationary in the tray while a user couples a threaded handle thereto.

Figure 16A:
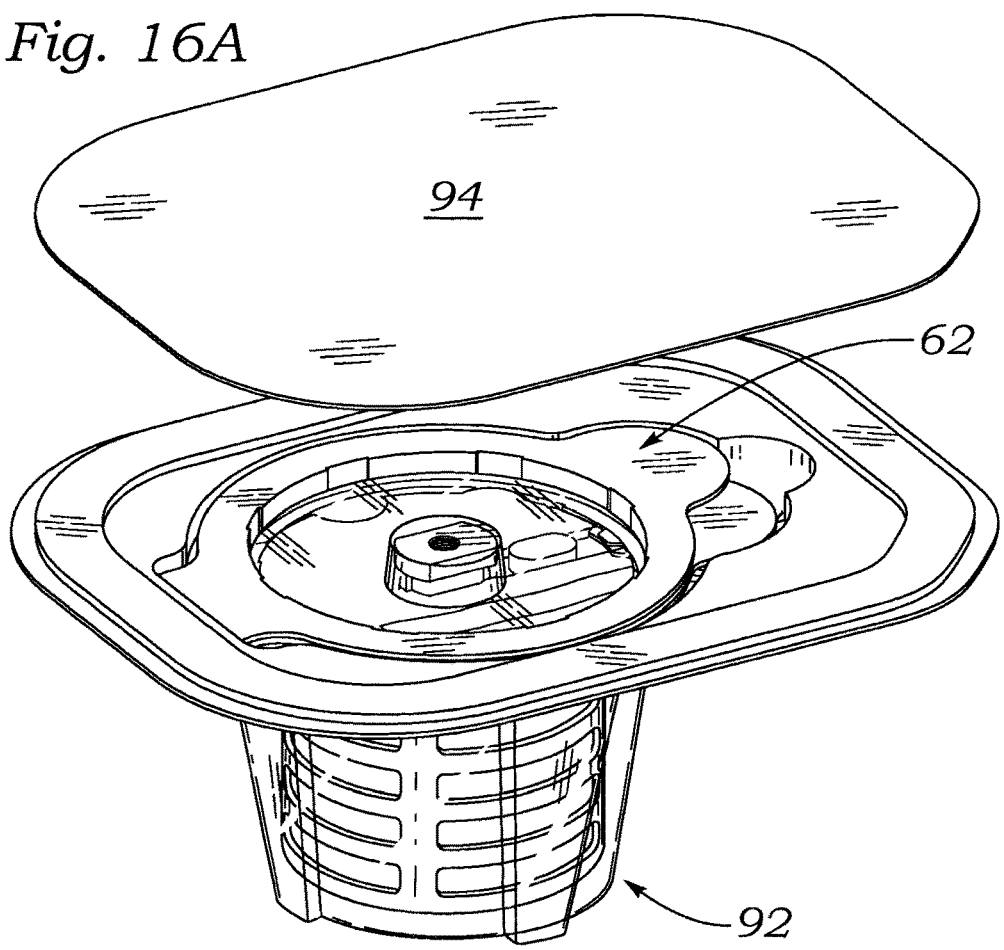
FIGS. 16A and 16B shows a gas-permeable lid positioned over and sealed to the storage tray having the mitral heart valve subassembly therein.
Figure 16B:
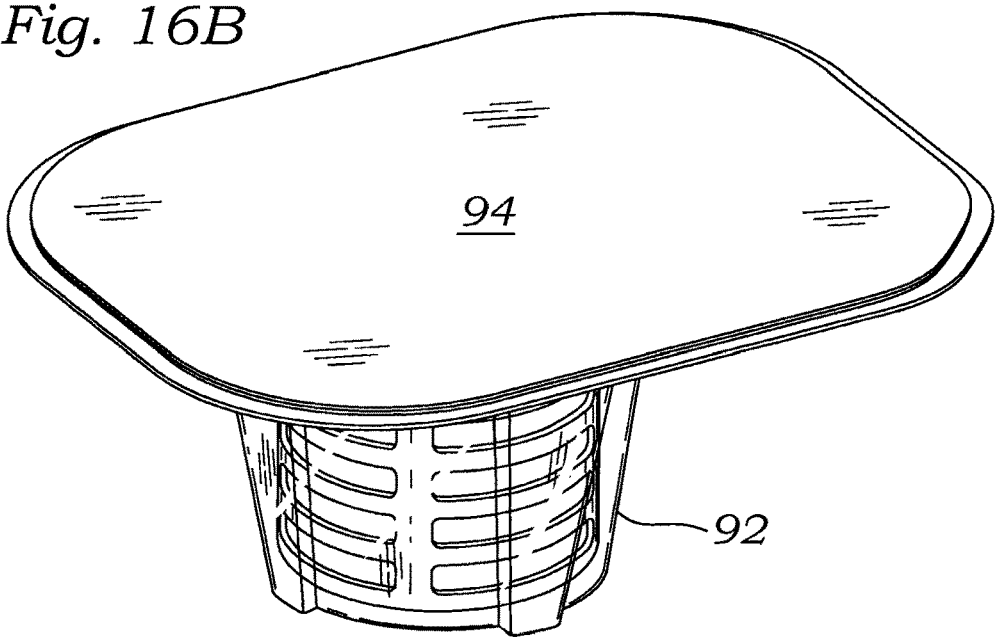

Once the mitral heart valve subassembly 110 has been positioned within the cavity of the storage tray 92, as in FIG. 15, and a cap such as the clam shell member 62 is snapped thereover, as in FIG. 16A, the gas-permeable lid 94 described above seals over an upper surface 96 of the tray 92, as in FIG. 16B. FIG. 15 shows the identification tag 124 which is visible through the clear plastic of the clam shell member 62 in FIG. 16A. At this stage, the assembly, and in particular the mitral heart valve therein, can be subjected to gas sterilization, such as with ETO.

The clam shell member 62 (or insert 130 for mitral valves) restricts rotation of the aortic or mitral valve holders, and therefore provides an efficient way of attaching a threaded handle to the holder while still in the packaging.

One advantage of the packaging solutions described herein is a double sterile barrier, wherein the inner and outer sterile containers allow for gas sterilization, such as with ETO, and with a second seal the outer sterile container also provides a barrier between the product and the surrounding atmosphere (e.g., oxygen) after sterilization. The inner sterile container has been described above, and for both aortic and mitral heart valves results in the sealed storage tray 92 shown in FIG. 16B. The sealed storage tray 92 is received within a secondary or outer container and the dual barrier assembly is then sterilized, so that there are redundant sterile barriers. Subsequently, the dual barrier assembly is sealed to prevent the outside air from reaching the heart valve, thus preventing oxygenation and potentially reducing calcification after implant. In the exemplary packaging sequence, the inner and outer containers are first assembled together and each closed with a gas-permeable barrier to form a dual barrier assembly which is gas-sterilized. Subsequently, the atmospheric barrier is added, such as by converting the outer container from being gas-permeable to being gas-impermeable. However, if the entire process is done in sterile conditions, such as in a clean room environment, the inner container may be closed and sterilized before being placed within the outer container, which is then closed and sterilized. In other words, there may be one or two sterilization steps prior to sealing the entire assembly against air ingress.

The present application describes two different secondary barriers—one a storage tray similar to that described earlier, and the other a flexible pouch. The secondary barrier protects and preserves the primary sterile barrier package in a sterile environment, and prevents oxygen from reaching the heart valve within A further outer shelf box may be used to facilitate temperature monitoring during distribution and storage, and protect the delicate implant from distribution hazards such as shock, impact and extreme temperatures.

FIGS. 17A-17C are orthogonal views of a secondary or outer storage tray 150 sized to receive the primary or inner storage tray 92. The secondary storage tray 150 desirably mimics the shape of the primary storage tray 92 such that the latter can be easily nest within a cavity 152 therein. As such, the storage tray 150 comprises an upper surface including a peripheral flange 154, and a container portion 156 extending downwardly therefrom having a stepped ledge 158 on an upper end and a lower trough 160. The inner walls of the container portion 156 define the cavity 152, and closely receive the inner storage tray 92.

The outer storage tray 150 provides a rigid secondary sterile barrier that protects and preserves the inner sterile barrier formed by the inner storage tray 92 and lid 94. Desirably, the outer storage tray 150 is constructed of a molded material, such as a polyethylene terephthalate copolymer (PETG). PETG is nominally gas-impermeable, though not entirely for the long-term storage needs described herein, perhaps years. The tray 150 instead may also be formed of a molded material that is gas-impermeable for the required time frame, though such materials may be somewhat more expensive than PETG. Once the sealed inner tray 92 is placed within the outer storage tray 150, a gas-permeable lid (not shown, but similar to lid 94 of the inner tray 92) seals against the flange 154 and permits sterilization gas (e.g., ETO) to reach the spaces within both trays.

Figure 11:
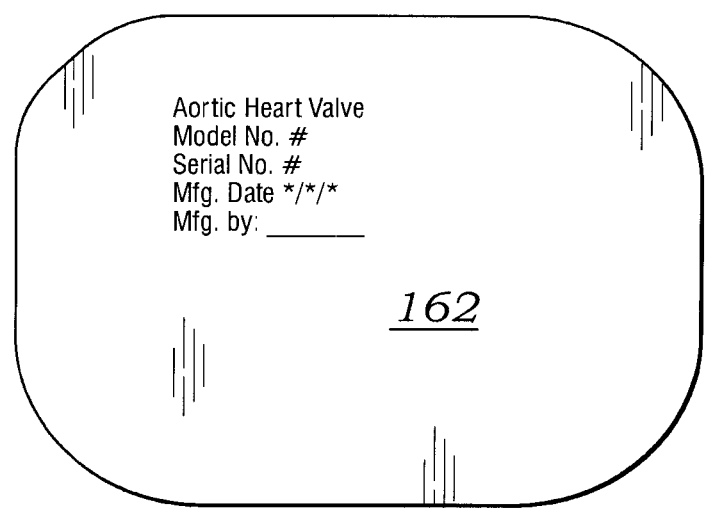
FIG. 11 is a plan view of an upper surface of a pressure sensitive foil label sized to cover storage trays disclosed herein and provide a gas-impermeable barrier for long-term storage of heart valves.

With reference back to FIG. 11, a gas-impermeable label 162 sized to cover the secondary storage tray 150 is shown. The label 162 is applied over the sterilized tray 150, and sealed on top of the lid. Once pressure adhered or heat sealed against the lid, the foil label 162 provides a complete barrier to gas transfer. The label 162 preferably includes a layer of metal foil laminated to a layer of a gas-permeable material such as DuPont 1073B Tyvek, or more preferably is a single layer of foil. The label 162 may have information printed thereon about the contents of the packaging, such as implant type, model, manufacturer, serial number, date of packaging, etc. A layer of pressure sensitive adhesive is provided to seal on top of the previously attached lid.

In an alternative configuration, as seen in FIG. 18, an outer storage tray 180 features a cavity 182 for receiving an inner tray surrounded by a double flange with an outer flange 184 offset from an inner flange 186. The inner flange 186 may first be sealed with a die-cut and heat seal adhesive coated gas-permeable lid (e.g., Tyvek) after placement of the inner sterile barrier package, enabling subsequent ETO sterilization of the entire package, and in particular the space between the two sterile barriers. A gas-impermeable label such as a single layer of foil is then sealed to the outer flange 184.

FIGS. 19A-19C show several potential configurations of the relative heights of the double flanges 184, 186 in the tray 180 of FIG. 18. In a preferred embodiment, both lids/labels applied to the flanges 184, 186 are attached with heat sealed adhesive for better long-term integrity of the bond. Heat sealing is typically accomplished by pressing down on the label with a heated surface such as a flat platen. However, heat and pressure should be applied only once to each flange seal to avoid affecting the seal integrity after formation, and a flat platen may require modification. There are several ways to manage this.

In a first embodiment of FIG. 19A, the flanges 184, 186 are at the same elevation. The gas-permeable lid or label is applied to the inner flange 186 using a heated press shaped the same as the flange. Alternatively, an insert shaped like the flange 186 may be introduced between a flat heated platen and the tray. After ETO sterilization, the foil label is applied to the outer flange 184 using a heated press shaped the same as the flange, or an insert shaped like the outer flange between a flat heated platen and the tray.

In FIG. 19B, the inner flange 186' elevates about the outer flange 184. In this configuration, a flat heated platen may be used to apply heat to an adhesive-coated label for the inner seal, while the outer seal is formed using a heated press shaped the same as the outer flange, or an insert shaped like the outer flange between a flat heated platen and the tray.

In FIG. 19C, the outer flange 184' elevates about the inner flange 186. In this configuration, the inner seal is first formed using a heated press shaped the same as the inner flange, or an insert shaped like the inner flange between a flat heated platen and the tray. Subsequently, a flat heated platen may be used to apply heat to an adhesive-coated foil label for the outer seal. The ability to use a flat heated platen for at least one of the seals simplifies the assembly apparatus and procedure.

Figure 20:
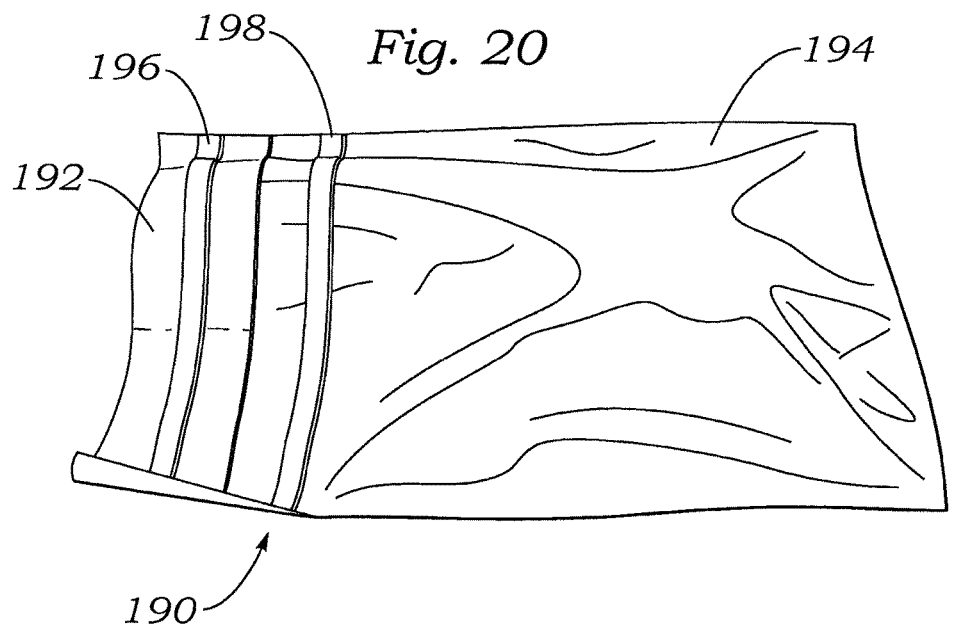
FIG. 20 is a plan view of an exemplary secondary storage pouch sized to receive the first storage tray.

FIG. 20 is a plan view of an exemplary secondary storage pouch 190 sized to receive the first storage tray 92, or inner sterile packaging. The storage pouch 190 includes a first gas-permeable portion 192 adjacent an open end (to the left), and a second, larger gas-impermeable portion 194 that is closed on the right end. The entire pouch 190 may be made of the gas-impermeable portion 194, except for a strip of the first portion 192 on the upper layer, or the first portion 192 may form both the upper and lower layers of the pouch adjacent the open end. A first seal 196 extends across the width of the open mouth of the pouch 190 in the area of the first gas-permeable portion 192. The second seal 198 also extends across the width of the pouch 190 but fully within the second gas-impermeable portion 194. During packaging, the first storage tray 92 is placed within the pouch 190 and the first seal 196 closed, at which time the entire contents are gas-sterilized. After the assembly is sterile, the second seal 198 is closed to prevent any further contact between the interior of the pouch 190 and the surrounding atmosphere.

Figure 21:
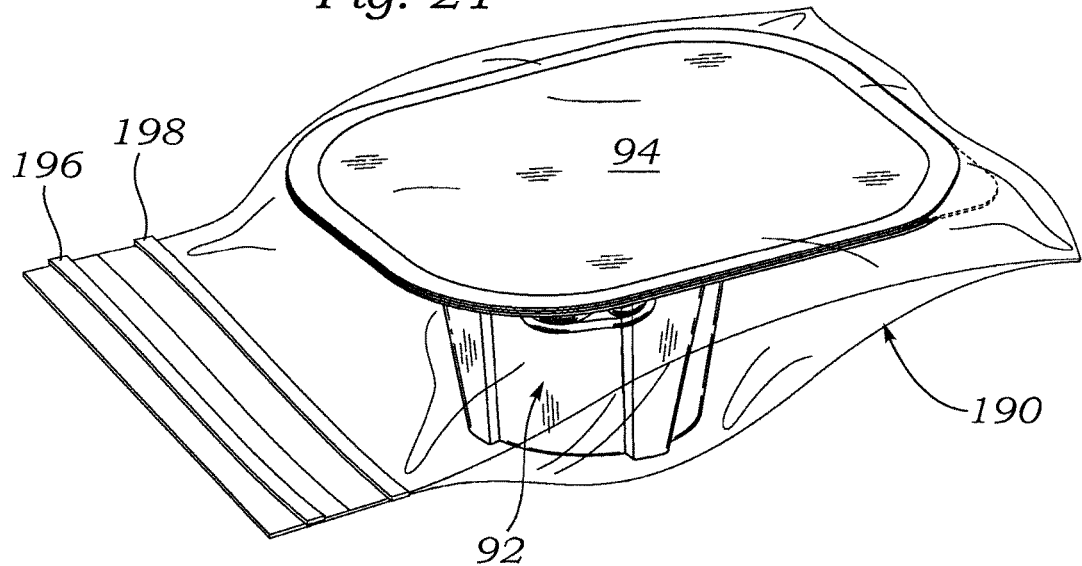
FIG. 21 is a perspective view of the first storage tray positioned within the secondary storage pouch, shown transparent.

FIG. 21 is a perspective view of the first storage tray 92 sealed with the lid 94 and positioned within the secondary storage pouch 190. The two seals 196, 198 enable gas sterilization of the contents of the pouch 190 prior to full sealing. More particularly, the first seal 196 may be closed at which time the package may be subject to ETO sterilization. Because the first seal 196 extends across the gas-permeable first portion 192, sterilizing gas can enter the interior of the pouch 190. After sterilization, second seal 198 is closed to prevent any further gas, in particular oxygen, from entering the interior of the pouch 190.

The storage pouch 190 provides a flexible secondary sterile barrier, and may be constructed of various materials or laminates having at least one gas-impermeable layer, with a foil/polyethylene fiber laminate being preferred. An inner layer of the foil material, such as available from Amcor, may feature a laminate of Low Density Polyethylene (LDPE) to facilitate seal under pressure and temperature. A tear notch on the pouch 190 may be provided for easy opening. With the second seal 198 closed, the foil pouch 190 provides an oxygen and moisture barrier after ETO sterilization.

Figure 22:
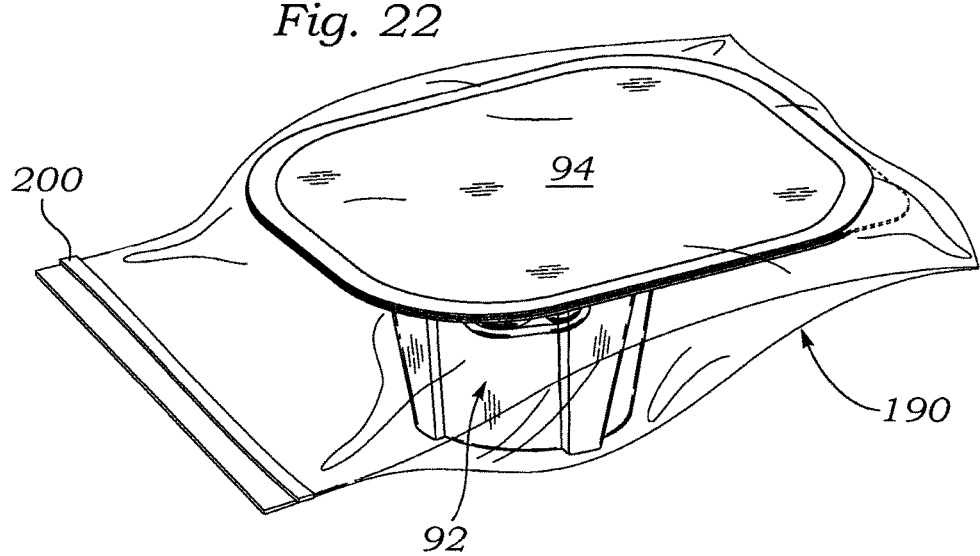
FIG. 22 is a perspective view of the first storage tray positioned within an alternative secondary storage pouch, shown transparent.
Figure 23:
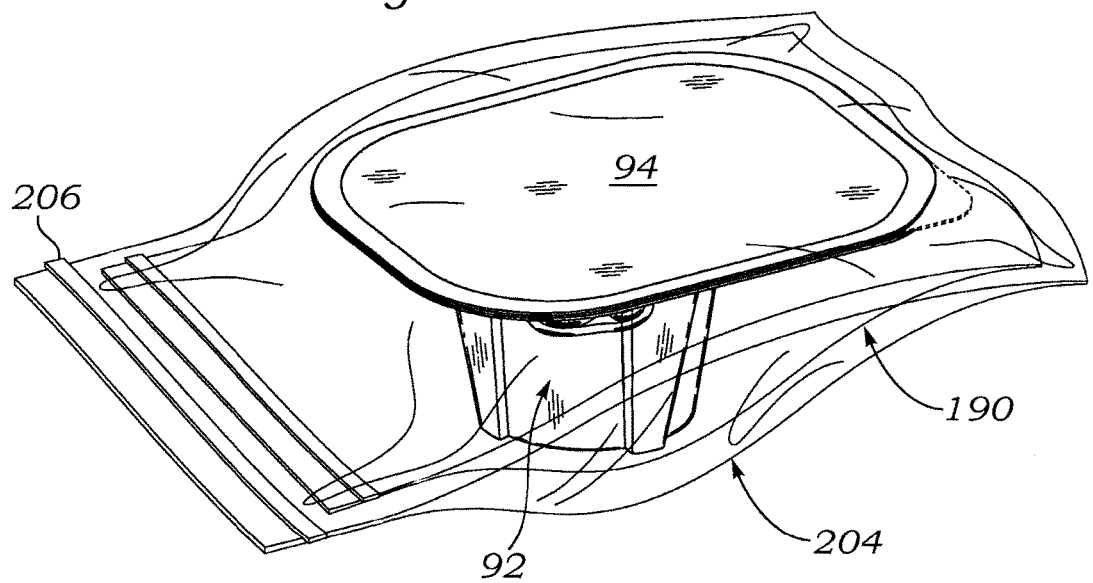
FIG. 23 is a perspective view of the assembly of FIG. 22 positioned within a tertiary storage container in the form of a pouch, shown transparent.

In an alternative configuration seen in FIG. 22, the secondary storage pouch 190 that receives the first storage tray 92 only includes a first gas-permeable seal 200. In use, the first storage tray 92 is placed within the secondary storage pouch 190 and the seal 196 closed, at which time the entire contents are gas-sterilized. After the assembly is sterile, the secondary storage pouch 190 and contents within are placed within a gas-impermeable tertiary container, such as pouch 204 in FIG. 23, to prevent any further contact between the interior of the pouch 190 and the surrounding atmosphere. The pouch 204 is desirably formed of gas-impermeable material and has a gas-impermeable seal 206.

In general, therefore, a preferred method includes stabilizing a dry prosthetic heart valve within a first gas-permeable container that provides some rigidity or protection from external damage. The first gas-permeable container and contents are then placed in a secondary gas-permeable container, and the entire assembly subjected to gas-based sterilization. Finally, the secondary container is sealed with a gas-impermeable barrier, such as by placing it within a gas-impermeable tertiary container to prevent gas transfer with the surrounding atmosphere.

In addition to the various embodiments of the double sterile packaging described above, the final packaging will typically include a shelf box, printed or unprinted, constructed of paperboard with a tamper-evident carton label as an indicator of the integrity of the package and placed in a foam box for insulation. Also, a temperature indicator for monitoring temperature during distribution and storage is attached to the shelf box.

The packaging solutions disclosed herein facilitate access to tissue implants, in particular prosthetic heart valves at the time of implantation. The process for removing the aortic valve 20 of FIG. 1 from its packaging will be described, though similar steps can be used to remove the mitral heart valve of FIGS. 12-16. The first step is removal of the outer or secondary sterile barrier, two embodiments of which have been described. One or both sealed labels over the outer tray 150, 180 are first detached, and the inner tray 92 sealed by the sterile lid 94 (seen in FIG. 16B) removed therefrom (alternatively, the technician tears open the pouch 190 of FIG. 21). At this stage, the inner sterile packaging may be transported to the immediate vicinity of the operation site without undue concern for the integrity of the package because of the relatively rigid inner tray 92 and sterile seal 94.

Subsequently, the technician detaches the lid 94, exposing the assembly seen in FIG. 8. The upper half 66 of the clam shell member 62 is lifted up from the lower half 64 to expose the generally circular clip 50 and valve holder 22, as seen in FIG. 5. A delivery handle (not shown) can then be threaded onto the holder, and the assembly of the valve 20, holder 22, and clip 50 removed from the clam shell member 62. Recall that the anti-rotation projection 78 of the clam shell member 62 engages the radial slot 56 of the clip 50 to prevent rotation of the clip in the clam shell member 62. This facilitates threading the handle onto the holder 22, such that the operation can be done with two hands. Finally, the clip 50 can easily be detached from the holder 22 by pulling it off laterally, leaving the valve 20 on the end of the delivery handle ready form implant.

The packaging assemblies herein provide a number of distinctive advantages to manufacturers of dry prosthetic valves, which advantages may also be transferred to the storage of other tissue implants that can be stored dry, such as dental implants, ligaments, vessel grafts, tissue patches or scaffolds, etc. Indeed, certain aspects of the present application can be utilized by makers of implants in general that are required to be stored in double sterile containers and which can be sterilized using a gas such as ETO. One advantage of the packaging described herein is that it contains and stabilizes the prosthetic heart valve. Movement of the heart valve within the storage container is detrimental as delicate tissue structures may be damaged if permitted to contact the sides of the packaging.

Due to presence of a gas-permeable sterile barrier such as a Tyvek Header (breathable vent) the product can easily be ETO sterilized and aerated for acceptable levels of residuals. After appropriate aeration time, the outer container, or second barrier, can be sealed (e.g., foil to foil) to prevent long term oxidation of the dry tissue valve.

The ETO sterilization obviates traditional oven sterilization, therefore reducing the amount of energy spent in heating the packaged product in an oven for multiple days. Similarly, elimination of autoclaving of the jars and closures before packaging will reduce the energy consumption required in the sterilization process.

As mentioned, the double sterile barrier allows for gas sterilization, such as with ETO, but also provides an oxygen barrier to the product after sterilization. Consequently, the entire assembly can be reliably stored in oxygen-free conditions for extended periods of time, even years, yet the outer sterile container can be removed at the time of use without exposing the contents of the inner sterile container to contaminants. The double layer of packaging enables sterile transfer of the inner package to the sterile operating field, and the inner package can even be temporarily stored for significant periods before the product is used. The new package design will be lighter in weight due to the choice of materials (PETG/Tyvek and air vs. Polypropylene with glutaraldehyde), which will reduce the shipping costs for single unit shipments.

Indeed, the biggest advantage over existing "wet" heart valve package designs is the elimination of storage and handling of liquid glutaraldehyde during the packaging and storage process, as well as the absence of glutaraldehyde at the time of use. This reduces hazards to the health of employees, customers, and patients, as well as the environment. Additionally, disposal of glutaraldehyde is bio-hazardous and therefore OSHA requires neutralization of the chemical before disposal or placement of appropriate controls for disposal. Due to decreased handling and critical storage requirements described herein, the packaging process is rendered less complex. The elimination of glutaraldehyde will not require an increased level of insulation from higher temperatures as the dry tissue valve already has the capability to withstand temperatures as high as 55° C. Therefore this will likely reduce the bulkiness of the design by reducing the size and insulation used for shipping the valve during summers and winters.

Current tissue valves available from Edwards Lifesciences are packaged in a 3.8 oz polypropylene jar/closure system with liquid glutaraldehyde. The presence of liquid glutaraldehyde requires the package design to maintain a state of temperature that will not overheat or freeze the tissue valve. Therefore the current package is bulky and heavier due to presence of EPS (Expanded Polystyrene) foam end caps outside the secondary package (shelf carton) which insulates from extreme temperature conditions. The polypropylene 3.8 oz jar/closure system with liquid glutaraldehyde, secondary package and foam insulation make the package design bulky and heavy resulting in increased space for storage and increased costs for shipping. The current single unit summer pack weighs approximately 0.85 lbs where as the current single unit winter pack weighs approximately 1.85 lbs. The packages disclosed herein are significantly lighter.

While the invention has been described in its preferred embodiments, it is to be understood that the words which have been used are words of description and not of limitation. Therefore, changes may be made within the appended claims without departing from the true scope of the invention.

What is claimed is:

1. A packaging assembly for storing a bioprosthetic heart valve without a liquid preservative solution, the packaging assembly comprising:
   a holder comprising an engagement structure configured for removably attaching a bioprosthetic heart valve, the holder comprising a shaft;
   a storage tray comprising a cavity;
   an insert sized to provide a cap over the cavity of the storage tray, the insert comprising a slot having a closed central end and an open outer periphery, the shaft of the holder being non-rotatably retained at the closed central end, wherein the insert defines a flat, generally planar disc comprising at least one of outward projections and flow passages; and
   wherein the packaging assembly does not comprise a liquid preservative solution.

2. The packaging assembly of claim 1, further comprising a cage comprising an upper end, the cage configured to at least partially enclose the bioprosthetic heart valve.

3. The packaging assembly of claim 2, wherein the cage is stored in the cavity of the storage tray.

4. The packaging assembly of claim 2, further comprising a clip member configured to be attached to the upper end of the cage, the clip member comprising a radial slot for receiving the shaft of the holder.

5. The packaging assembly of claim 3, wherein the storage tray comprises a stepped ledge to suspend the cage within the cavity.

6. The packaging assembly of claim 5, wherein the insert comprises outward projections and the storage tray comprises corresponding internal features and wherein the outward projections engage the internal features of the storage tray to limit rotational movement of the insert when positioned on the stepped ledge.

7. The packaging assembly of claim 5, wherein the insert comprises flow passages and the storage tray comprises flow channels and wherein the flow passages align with the flow channels when the insert is positioned on the stepped ledge.

8. The packaging assembly of claim 1, wherein the engagement structure of the holder comprises attachment sutures configured for removably attaching to a sewing ring of the heart valve.

9. The packaging assembly of claim 1, wherein the holder comprises an upper bore having internal threads configured for attaching a delivery handle.

10. The packaging assembly of claim 1, wherein the storage tray comprises flow channels.

11. The packaging assembly of claim 1, wherein the insert comprises both outward projections and flow passages.

12. The packaging assembly of claim 1, further comprising a gas-permeable lid configured to seal an open end of the storage tray.

13. A packaging assembly for storing a bioprosthetic heart valve without a liquid preservative solution, the packaging assembly comprising:
a holder comprising an engagement structure configured for removably attaching a bioprosthetic heart valve, the holder comprising a shaft and an upper bore having internal threads configured for attaching a delivery handle;
a storage tray comprising a cavity and flow channels;
an insert sized to provide a cap over the cavity of the storage tray, the insert comprising a slot having a closed central end and an open outer periphery, the shaft of the holder being non-rotatably retained at the closed central end, wherein the insert defines a flat, generally planar disc comprising both outward projections and flow passages; and
wherein the packaging assembly does not comprise a liquid preservative solution.

14. The packaging assembly of claim 13, further comprising a cage comprising an upper end, the cage configured to at least partially enclose the bioprosthetic heart valve.

15. The packaging assembly of claim 14, wherein the cage is stored in the cavity of the storage tray.

16. The packaging assembly of claim 14, further comprising a clip member configured to be attached to the upper end of the cage, the clip member comprising a radial slot for receiving the shaft of the holder.

17. The packaging assembly of claim 15, wherein the storage tray comprises a stepped ledge to suspend the cage within the cavity.

18. The packaging assembly of claim 17, wherein the insert comprises outward projections and the storage tray comprises corresponding internal features and wherein the outward projections engage the internal features of the storage tray to limit rotational movement of the insert when positioned on the stepped ledge.

19. The packaging assembly of claim 13, wherein the engagement structure of the holder comprises attachment sutures configured for removably attaching to a sewing ring of the heart valve.

20. The packaging assembly of claim 13, further comprising a gas-permeable lid configured to seal an open end of the storage tray.

* * * * *